United States Patent [19]

Bruzzese et al.

[11] 4,192,864
[45] Mar. 11, 1980

[54] METHOD FOR THE TREATMENT OF DYSLIPIDAEMIA AND ARTERIOSCLEROSIS

[75] Inventors: Tiberio Bruzzese; Lorenzo Ferrari, both of Milan, Italy

[73] Assignee: Prospa N.V., Curacao, Netherlands Antilles

[21] Appl. No.: 910,951

[22] Filed: May 30, 1978

[30] Foreign Application Priority Data

May 30, 1977 [GB] United Kingdom ............... 22736/77

[51] Int. Cl.² .......................................... A61K 35/00
[52] U.S. Cl. .................................................. 424/122
[58] Field of Search ......................................... 424/122

[56] References Cited

U.S. PATENT DOCUMENTS

| | | | |
|---|---|---|---|
| 3,773,925 | 11/1973 | Bruzzese et al. | 424/122 |
| 3,780,173 | 12/1973 | Bruzzese et al. | 424/122 |
| 3,961,047 | 6/1976 | Bruzzese et al. | 424/122 |
| 3,961,048 | 6/1976 | Dell'Acqua et al. | 424/122 |
| 4,014,994 | 3/1977 | Maghaghi et al. | 424/122 |
| 4,017,603 | 4/1977 | Ferrari et al. | 424/122 |

*Primary Examiner*—Jerome D. Goldberg
*Attorney, Agent, or Firm*—Wenderoth, Lind & Ponack

[57] ABSTRACT

The present invention is concerned with a method for the treatment of dyslipidaemia and arteriosclerosis in human beings, comprising administering an effective amount of an active compound selected from the group consisting of partricin, alkyl esters of partricin and alkyl esters of N-mono- or disubstituted partricin to a human being in need of said treatment. If desired, the active compound can be administered in the form of a water-soluble complex with a compound selected from the group consisting of benzalkonium chloride, sodium lauryl sulphate, sodium tetradecyl sulphate, sodium desoxycholate and sodium dehydrocholate.

2 Claims, No Drawings

METHOD FOR THE TREATMENT OF DYSLIPIDAEMIA AND ARTERIOSCLEROSIS

BACKGROUND OF THE INVENTION

In U.S. Pat. Nos. 3,773,925 and 3,780,173, there are described and claimed, respectively, a new polyene antibiotic (partricin) and its methyl ester and the preparations thereof, both of which have a marked anti-infective activity on protozoa and pathogenic fungi in mammals and plants. Such activity has shown to be of particular value in treating infections caused by *Trichomonas vaginalis* and/or *Candida albicans* in humans. For reasons of toxicity, which are not separate from those of activity, in human pathology, the methyl ester of partricin, which is known as mepartricin (USAN) is currently used; other alkyl esters of partricin which have been prepared include the ethyl, propyl and butyl esters, as well as the alkyl esters of N-mono and disubstituted partricin, such as diacetyl partricin, dipropionyl partricin, dibutyryl partricin and disuccinyl partricin, which, together with the preparation thereof, are described and claimed in U.S. Pat. No. 3,961,047 and in pending U.S. Patent Application No. 839,509 filed the 4th October, 1977. Furthermore, water-soluble complexes of partricin and of alkyl esters thereof have been disclosed in U.S. Pat. Nos. 3,961,048 and 4,017,603.

The active compounds contemplated in the present invention include partricin, $C_1-C_6$ esters of partricin and $C_1-C_6$ esters of N-mono- and disubstituted partricin wherein the N-substituents are $C_1-C_6$ alkyl or $C_1-C_6$ carboxylic acyl.

From a biological point of view, these derivatives have also shown particular activity against protozoa and pathogenic fungi.

SUMMARY OF THE INVENTION

We have now found experimentally and clinically that partricin and its derivatives, following oral administration, are able notably to reduce the blood cholesterol and triglyceride levels, with obvious therapeutic advantages in cases of dyslipidaemia or arteriosclerosis.

DETAILED DESCRIPTION OF THE INVENTION

Medical research has paid considerable attention over the past ten years, and today even more so, to the plasma lipids; this considerable increase of interest in fats in the blood is largely due to the direct correlation which exists between the plasma concentration of lipids and the risk of death from cardiovasculopathies or, at any rate, serious debilitating forms with cardiovasculopathic involvement.

This correlation was first demonstrated by comparing the incidence of coronary cardiopathies with the average concentration of plasma cholesterol in adults from different parts of the world. For example, it was found that in the non-urban communities of Africa, where death from infarct or coronaropathy is practically unheard of, the average plasma cholesterol concentration is about 100 mg./100 ml. less than that present in white Americans of the same age.

More detailed investigations have demonstrated statistically that, within populations, the likelihood of an individual having a myocardial infarct is directly related to his plasma cholesterol concentration.

It has not yet been fully demonstrated that this possible correlation is the equivalent of a cause and effect association and it will certainly take many years before this complicated problem can be answered. Nevertheless, many circumstantial trials suggest that an elevated cholesterol concentration in the plasma does not simply represent an "index" of an increased risk of coronary disease but that cholesterol, when present in excessive plasma conditions, is, in itself, a cause of the atheromatous lesions which are predisposing factors in coronary diseases. The same correlation would seem to be valid for the plasma triglycerides.

It must be borne in mind, however, that most of the cholesterol present in the atheromatous plaques in man seems to penetrate into the lesion from the very low-density plasma proteins, which represent the main lipoprotein vectors of plasma cholesterol in man. Furthermore, premature death from coronaropathy is inevitable in serious forms of inherited hypercholesterolaemia. Finally, it is to be remembered that many experimental procedures which determine an increase in the plasma cholesterol concentration in non-human primates, produce vascular lesions similar to those seen in coronary disease in man.

Therefore, the study of substances which are able to act on hyperdyslipidaemias is of particular practical interest not only for immediate clinical activity but especially to contain and delay the onset of atherosclerotic cardiovascular phenomena.

Since we have found that partricin and its above-mentioned derivatives act on the lipid monolayers, binding themselves to the cholesterol fraction (as monitored spectrophotometrically), mepartricin, as test substance, was administered orally in the pharmaceutical forms (later specified) to ascertain whether it had an effect on lipid metabolism, particularly at the level of cholesterol, of triglycerides.

Mepartricin, at a dose of 2 tablets per day of 50,000 Units each was administered for 15 days to 33 subjects (13 male, 20 female) with an average age of 56.94 years. All the subjects had a dyslipaemic condition, verified by laboratory tests, with particular regard to total lipidaemia and total cholesterolaemia. A dietary regimen was prescribed for all the patients.

For the study of the systemic tolerance, haematochemical constants were examined (haemochromocytometry, azotaemia, glycaemia, bilirubinaemia, serum glutamic oxaloacetic transaminase (SGOT) and serum glutamic pyruvic transaminase (SGPT)) and also the urinary constants, the values being determined before and at the end of the trial.

The data obtained were elaborated statistically with the Student t test. The following Table 1 gives the individual values of the tests carried out at the established times. As can be seen, in all subjects treated with mepartricin, a notable decrease in the total lipaemia and cholesterolaemia values was ascertained after 15 days.

The statistical analysis (Student t) carried out on the numerical indices of the parameters shows that the decrease reaches a highly significant level.

TABLE I

Influence of mepatricin on some lipaemic parameters.

| Case No. | Patients' initials | Age | Sex | Total lipidaemia (mg/100 ml.) | | | Total cholesterolaemia (mg/100 ml.) | | |
|---|---|---|---|---|---|---|---|---|---|
| | | | | Determinations carried out 10 days before treatment | Initial determinations | Determinations carried out at the end of treatment | Determinations carried out 10 days before treatment | Initial determinations | Determinations carried out at the end of treatment |
| 1 | F.P.A. | 48 | M | 1000 | 1000 | 700 | 225 | 225 | 175 |
| 2 | C.M. | 42 | M | 900 | 840 | 550 | 255 | 250 | 175 |
| 3 | B.G. | 70 | M | 900 | 900 | 550 | 210 | 210 | 180 |
| 4 | B.A. | 40 | M | 950 | 900 | 625 | 240 | 240 | 190 |
| 5 | Z.A. | 58 | M | 800 | 720 | 500 | 240 | 230 | 165 |
| 6 | N.M. | 61 | M | 700 | 640 | 580 | 215 | 210 | 130 |
| 7 | B.A. | 60 | M | 700 | 700 | 700 | 250 | 255 | 190 |
| 8 | P.R. | 53 | F | 850 | 830 | 800 | 230 | 230 | 190 |
| 9 | Z.A. | 44 | F | 900 | 900 | 600 | 210 | 200 | 180 |
| 10 | C.P. | 70 | F | 800 | 800 | 550 | 225 | 220 | 170 |
| 11 | M.P. | 56 | F | 1200 | 1250 | 1240 | 320 | 320 | 285 |
| 12 | M.G. | 24 | M | 1200 | 1200 | 1000 | 310 | 310 | 235 |
| 13 | C.R. | 41 | M | 1300 | 1250 | 840 | 300 | 295 | 240 |
| 14 | D.F.R. | 48 | M | 1100 | 1000 | 900 | 290 | 290 | 230 |
| 15 | Z.A. | 50 | M | 800 | 800 | 600 | 310 | 300 | 230 |
| 16 | D.E. | 54 | F | 1000 | 1000 | 900 | 290 | 285 | 240 |
| 17 | T.A. | 64 | F | 800 | 700 | 550 | 340 | 340 | 235 |
| 18 | M.G. | 71 | F | 1000 | 1000 | 1000 | 290 | 285 | 220 |
| 19 | B.G. | 72 | F | 850 | 800 | 480 | 360 | 360 | 220 |
| 20 | P.G. | 45 | F | 1000 | 1000 | 980 | 320 | 320 | 210 |
| 21 | A.B. | 33 | M | 1000 | 940 | 650 | 310 | 300 | 235 |
| 22 | O.A. | 63 | F | 850 | 830 | 750 | 350 | 350 | 255 |
| 23 | F.D. | 76 | M | 920 | 900 | 850 | 290 | 280 | 130 |
| 24 | B.M. | 70 | F | 1200 | 1150 | 1000 | 280 | 280 | 180 |
| 25 | S.L. | 52 | F | 1000 | 1000 | 1000 | 290 | 280 | 170 |
| 26 | S.M. | 58 | F | 1000 | 1000 | 900 | 312 | 299 | 281 |
| 27 | C.A. | 60 | F | 1150 | 1200 | 900 | 310 | 304 | 291 |
| 28 | B.H. | 65 | F | 1250 | 1250 | 850 | 292 | 298 | 260 |
| 29 | C.A. | 65 | F | 1000 | 1000 | 950 | 269 | 280 | 251 |
| 30 | S.B. | 65 | F | 1200 | 1250 | 700 | 289 | 296 | 211 |
| 31 | B.R. | 73 | F | 900 | 900 | 750 | 265 | 271 | 187 |
| 32 | C.M. | 65 | F | 950 | 950 | 900 | 265 | 262 | 261 |
| 33 | B.W. | 63 | F | 1100 | 1150 | 850 | 295 | 292 | 251 |
| | $\bar{x}$ | | | 977.87 | 962.12 | 778.63 | 280.21 | 277.78 | 213.72 |
| | s.d. | | | ±157.89 | 174.56 | ±186.36 | ± 40.28 | ± 40.70 | ± 42.14 |

It can be seen that the lipaemia value dropped from an initial average value of 962.12 mg/100 ml. ±174.56 to 778.63 mg/100 ml. ±186.36 at the end of the treatment, resulting in a t value equal to 5.837 ($P<0.01$). With regard to cholesterolaemia, the final average value was 213.72±42.14 mg/100 ml. against an initial average value of 277.78±40.70 mg/100 ml., the value of t being 8.883 ($P<0.01$).

Tolerance was excellent in all cases, as is demonstrated by the following haematochemical data:

TABLE 2

Mean values of haematochemical indices before (B) and after (A) treatment

| Cases | Erythrocytes ($\times$ mm$^3$) | | Leukocytes ($\times$ mm$^3$) | | Azotaemia (mg % ml) | | Glycaemia (mg % ml) | |
|---|---|---|---|---|---|---|---|---|
| 33 | B | A | B | A | B | A | B | A |
| $\bar{x}$ | 4.305,000 | 4,325,333 | 6,915 | 6,800 | 33.12 | 33.21 | 75.20 | 75.33 |
| s.d. | ±75515.28 | ±86220.02 | ±873.20 | ±825.31 | ±1.58 | ±1.66 | ±2.47 | ±2.81 |

| Cases | Bilirubinaemia (mg % ml) | | SGOT (U % ml) | | SGPT (U % ml) | |
|---|---|---|---|---|---|---|
| 33 | B | A | B | A | B | A |
| $\bar{x}$ | 0.41 | 0.39 | 11.13 | 12.02 | 10.06 | 11.68 |
| s.d. | ±0.02 | ±0.02 | ±0.90 | ±1.02 | ±1.13 | ±1.52 |

The new method of treating hyperdyslipidaemias according to the present invention is based on the oral administration of mepatricin or of other derivatives of partricin, the activity of which in this field is very similar.

The formulations described in the following Examples are given for the purpose of illustrating the present invention:

EXAMPLE 1

Each tablet contains:

| | |
|---|---|
| partricin methyl ester | 50,000 U |
| starch | 40 mg. |
| sodium citrate | 30 mg. |
| talc | 10 mg. |
| magnesium stearate | 5 mg. |
| lactose | q.s. ad 280 mg. |

EXAMPLE 2

Each gastroresistant tablet contains:

| | |
|---|---|
| partricin methyl ester | 50,000 U |
| starch | 40 mg. |
| sodium citrate | 30 mg. |
| talc | 10 mg. |
| magnesium stearate | 5 mg. |
| lactose | q.s. ad 280 mg. |
| shellac | 1.5 mg. |
| cellulose acetate phthalate | 9 mg. |
| diethyl phthalate | 5.5 mg. |

EXAMPLE 3

One gram of granulate for an oral suspension contains:

| | |
|---|---|
| partricin methyl ester | 50,000 U |
| sodium citrate | 0.03 g. |
| precipitated silica | 0.01 g. |
| sodium carboxymethylamide | 0.09 g. |
| cocoa powder | 0.01 g. |
| cocoa fluid extract | 0.01 g. |
| powdered sucrose | q.s. ad 1 g. |

Water is added to the dry granulate powder (25 ml. per 5 g. of product); thus, 1 ml. of oral suspension contains 10,000 U of mepartricin.

For the purposes of the present invention, it can be useful to administer mepartricin, or other derivatives of partricin, in a solubilised form, combined with a surfactant, for example, benzalkonium chloride, sodium lauryl sulphate, sodium tetradecylsulphate, sodium desoxycholate or sodium dehydrocholate (see U.S. Pat. Nos. 3,961,048 and 4,017,603).

EXAMPLE 4

Each gastroresistant tablet contains:

| | |
|---|---|
| mepartricin/Na lauryl sulphate complex | 50,000 U |
| starch | 40 mg. |
| sodium chloride | 30 mg. |
| sodium citrate | 30 mg. |
| magnesium stearate | 5 mg. |
| microgranular cellulose | 360 mg. |
| gastroresistant coating | q.s. ad 385 mg. |

The compositions described in the above Examples are for administration to human beings requiring treatment for dyslipidaemia or arteriosclerosis.

The present invention is not limited to the above described pharmaceutical formulations. Thus, for example, for oral administration, use can be made of all types of dosage units, such as tablets, dragees, hard gelatine capsules, syrups and the like.

We claim:

1. A method for the treatment of dyslipidaemia and arteriosclerosis in human beings, comprising administering methyl partricin to a human being in need of said treatment in an amount sufficient to effectively alleviate dyslipidaemia or arteriosclerosis.

2. A method according to claim 1, wherein the methyl partricin is used in the form of a water-soluble complex with a compound selected from the group consisting of benzalkonium chloride, sodium lauryl sulphate, sodium tetradecyl sulphate, sodium desoxycholate and sodium dehydrocholate.

* * * * *